(12) United States Patent
Feng et al.

(10) Patent No.: US 8,882,827 B2
(45) Date of Patent: Nov. 11, 2014

(54) STENT

(75) Inventors: Hai Quan Feng, Inner Mongolia (CN); Suguru Kishimoto, Okayama (JP); Jun Kubota, Kawasaki (JP); Minoru Asahara, Kurashiki (JP)

(73) Assignee: Japan Stent Technology Co., Ltd., Okayama (JP)

( * ) Notice: Subject to any disclaimer, the term of this patent is extended or adjusted under 35 U.S.C. 154(b) by 35 days.

(21) Appl. No.: 13/395,581

(22) PCT Filed: Sep. 16, 2010

(86) PCT No.: PCT/JP2010/066100
§ 371 (c)(1),
(2), (4) Date: Mar. 12, 2012

(87) PCT Pub. No.: WO2011/034154
PCT Pub. Date: Mar. 24, 2011

(65) Prior Publication Data
US 2012/0172974 A1     Jul. 5, 2012

(30) Foreign Application Priority Data
Sep. 17, 2009   (JP) .................................. 2009-215464

(51) Int. Cl.
*A61F 2/06* (2013.01)
*A61F 2/915* (2013.01)
(52) U.S. Cl.
CPC ....... *A61F 2/915* (2013.01); *A61F 2002/91558* (2013.01)
USPC ....................................................... 623/1.16

(58) Field of Classification Search
USPC ........ 623/1.11, 1.15–1.2, 1.39; 606/108, 191, 606/194, 198, 200
See application file for complete search history.

(56) References Cited

U.S. PATENT DOCUMENTS

| | | | |
|---|---|---|---|
| 6,017,365 A | 1/2000 | Von Oepen | |
| 7,179,285 B2 | 2/2007 | Ikeuchi et al. | |
| 7,985,251 B2 | 7/2011 | Ikeuchi et al. | |

(Continued)

FOREIGN PATENT DOCUMENTS

| | | |
|---|---|---|
| CN | 101357089 A | 2/2009 |
| EP | 1/277/489 B1 | 1/2014 |

(Continued)

OTHER PUBLICATIONS

Machine translation from JPO of WO 2008/126894, Oct. 23, 2008.*

(Continued)

*Primary Examiner* — Katherine M Shi

(57) ABSTRACT

The stent comprises a tubular body comprising a plurality of ring units arranged in the axis direction and bridged by a connecting element. Each of the units comprises a plurality of cells connected with each other, each of the cells having a U-shaped form comprising two linear parts and a circular arc part therebetween, and opening toward one end. The ring units comprise first and second units alternatively arranged and the oppositely disposed cells of the first and second units are only partly bridged by the connecting elements. The shapes of the cells of the first and second units are axisymmetrical about the connecting element. The curvature radius of the top of the arc constituting the arc part is 1.1 and 1.5 times larger than that of each of the tangent circles formed at the edges of two linear parts of the cell on the circular arc part side.

8 Claims, 5 Drawing Sheets

(56) References Cited

U.S. PATENT DOCUMENTS

| | | | |
|---|---|---|---|
| 2003/0158596 A1 | 8/2003 | Ikeuchi et al. | |
| 2005/0015136 A1 | 1/2005 | Ikeuchi et al. | |
| 2006/0276877 A1* | 12/2006 | Owens et al. | 623/1.15 |
| 2007/0010869 A1 | 1/2007 | Sano | |
| 2007/0021827 A1* | 1/2007 | Lowe et al. | 623/1.16 |
| 2007/0055353 A1* | 3/2007 | Fliedner | 623/1.16 |
| 2009/0105809 A1* | 4/2009 | Lee et al. | 623/1.17 |
| 2010/0004735 A1* | 1/2010 | Yang et al. | 623/1.16 |
| 2010/0249904 A1 | 9/2010 | Takayuki et al. | |
| 2010/0262227 A1* | 10/2010 | Rangwala et al. | 623/1.16 |

FOREIGN PATENT DOCUMENTS

| | | |
|---|---|---|
| JP | 3654627 | 3/2005 |
| JP | 3663192 | 4/2005 |
| JP | 3145720 | 9/2008 |
| JP | 2009-82245 | 4/2009 |
| WO | WO 2008/126894 A1 | 10/2008 |

OTHER PUBLICATIONS

International Search Report for PCT/JP2010/066100 mailed Dec. 21, 2010.

International Preliminary Report on Patentability mailed Apr. 19, 2012 issued in corresponding International Patent Application No. PCT/JP2010/066100.

Chinese Office Action mailed Jan. 22, 2014 in corresponding Chinese Application No. 201080041220.9.

Japanese Office Action mailed Apr. 22, 2014 in corresponding Japanese Application No. 2011-531975.

Chinese Office Action dated Aug. 12, 2014 in corresponding Chinese Patent Application No. 201080041220.9.

Extended European Search Report dated Jun. 16, 2014 in corresponding European Patent Application No. 10817267.7.

* cited by examiner

STENT

CROSS REFERENCE TO RELATED APPLICATIONS

This application claims the benefit under 35 U.S.C. Section 371, of PCT International Application No. PCT/JP2010/066100, filed Sep. 16, 2010, which claimed priority to Japanese Application No. 2009-215464, filed Sep. 17, 2009 in the Japanese Patent Office, the disclosures of which are hereby incorporated by reference.

FIELD OF THE INVENTION

The present invention relates to a stent used in order to reduce stenosis of an aperture, such as a blood vessel, in the living body, and in particular, relates to a stent which is excellent in durability and has a bending flexibility.

In the practice of the present invention, the term "stent" referred to hereinabove and hereinafter is intended to mean an instrument formed from a biocompatible material, the instrument which is used to expand an aperture, such as a blood vessel, in the living body and to maintain the size of the aperture to be expanded.

In general, a stent is introduced to a desired aperture position in the body with an inflation-type balloon. As the balloon is inflated, the stent is also expanded to reopen the aperture where stenosis occurs.

BACKGROUND ART

As a conventionally stent structure, a stent shown in FIG. 7 (a structure described in FIG. 1 of Patent Documents 1 and 2) has been known. In the stent described in Patent Documents 1 and 2, a plurality of cells 11 have been connected with each other in the circumferential direction to be arranged so that the central axis C1 of the stent 15 is surrounded to constitute a ring unit 12. Each of the opposing cells 11 and 11' of the adjacent ring units 12 and 12', respectively, is bridged by a connecting element 14 having an approximately or substantially S shape.

Moreover, as other stent structures, structures shown in FIGS. 3 and 5 (structures described in FIGS. 1 and 3 of Patent Document 3) have been known. These stents include a first ring unit 8 comprising a first cell group in which a plurality of first cells 7 are connected with each other in the circumferential direction and a second ring unit 8' comprising a second cell group in which a plurality of second cell 7' are connected with each other in the circumferential direction so that the first and second ring units are alternatively arranged to surround the central axis C1 of the stent 6. The first and second cells in the adjacent first and second ring units 8 and 8', respectively, are disposed oppositely and some (not all) of the first and second cells are bridged by a connecting element 9. The shapes of the first and second cells 7 and 7' are axisymmetrical of the stent 6 about the connecting element 9. The cell with a bridged part formed of the above-mentioned connecting element 9 is slightly longer than the cells which are not bridged with each other.

Furthermore, referring to a stent 1 (S-Stent) shown in FIG. 8 which is produced and available from another company, cells 16 and 16' are partially bridged by the connecting element 17 and have a constant length. The connecting element 17 is about 0.2 mm in length. In a stent 2 (Driver) shown in FIG. 9 which is produced and available from another company, cells 18 and 18' are formed from CoCr alloy wire which is bent in the shape of zigzag, and some of the oppositely disposed cells are bridged by a connecting element 19 through welding.

PATENT DOCUMENT

[Patent Document 1] JP Patent No. 3654627
[Patent Document 2] JP Patent No. 3663192
[Patent Document 3] JP utility model registration No. 3145720

DISCLOSURE OF THE INVENTION

Problems to be Resolved by the Invention

In recent years, stent treatment has become widely and rapidly used and served as good news for patients. In the treatment, an affected portion (or lumen) of artery which became narrow by advance of arteriosclerosis is expanded mechanically with a balloon catheter and a metal stent is placed in the lumen so as to recover the blood flow of the artery. The stent used for this treatment needs to satisfy the following three requirements. In the first place, a compressed stent is mounted around a balloon which is attached to the distal end of a balloon catheter, and is allowed to be passed through a patient's winding artery to be conveyed to a lesion part or a stenosis part while passing along a guide wire which was inserted into the artery in advance. Accordingly, such a stent must be flexible in order to pass through a winding and narrow artery. In the second place, the stent in the expanded state needs to have strength sufficient for supporting an artery wall or maintaining a stenosis part in the dilation. Furthermore, in spite that the stent receives repeated bending loads according to the beat of the heart, it must have durability to withstand the load. In the third place, when the stent is expanded by inflating the balloon of a balloon catheter, the full length of the stent after expansion becomes shorter than the length in the compressed state. If the length of the expanded stent becomes short, such a short stent may fail to cover an affected area as planned by a doctor. Accordingly, it is desirable that there is little change in length of the stent before and after expansion.

As a result of intensive studies conducted by the inventors of the present invention, the inventors found that the stents disclosed by Patent Documents 1 and 2 had uniform flexibility and sufficient strength to maintain the dilation of a stenosis part, whereas they had the following disadvantages. That is, the finite element analysis revealed that when such stents received a bending load, the maximum stress occurred at the top of the bending part 13 constituting an S-shaped connecting element. Further, the results of a fatigue durability test showed that the bending durability of the top of the bending part 13 was inferior to the bending durability of cells 11 and 11' disposed oppositely as well as bending durability of substantially linear part which constituted S-shaped connecting element. From the viewpoint of durability in the stent treatment, it should be avoided that excessive stress occurs at the top of the arc constituting the bending part 13 when the stent is subjected to very complicated deformation loads such as bending and torsion in a blood vessel. Therefore, the stents disclosed by Patent Documents 1 and 2 still remain the problems to be solved at this point.

Evaluation of physical properties of stent described in Patent Document 3 revealed that although the stent had sufficient bending durability when a bending load was received, this stent was hardly expansible because of its higher standard distension pressure at the time of stent expansion than those of stents disclosed in Patent Documents 1 and 2, for example the stent in FIG. 7 of Patent Document 2. Therefore, there is a subject in respect of expansibility in the stent disclosed in Patent Document 3. Moreover, as is the case with the stent disclosed in Patent Document 3, stents commercially available from other companies shown in FIGS. 8 and 9 also have an inadequate expansibility.

Therefore, the object of the present invention is to provide a stent having a high flexibility which can be easily conveyed through winding thin artery, being excellent in expansibility at the time of expansion, having sufficient strength to maintain the dilation of a stenosis part in support of an artery wall, and being excellent in durability which bears the repetitive bending load of the artery resulting from the heart beat.

Means of Solving the Problems

As a result of intensive studies conducted by the inventors of the present invention with respect to the bending durability of the substantially circular arc part of a cell, it has been finally found that (i) the maximum stress in substantially circular arc part of the cell occurs at the time of the stent expansion by the balloon as well as under the repetitive bending load of the heart beat after placement of the stent, and the strength of the maximum stress greatly depends on the structure of the connecting element of the cell and that (ii) optimization of the structure of the connecting element between cells disposed oppositely greatly raises a bending durability, without spoiling expansibility.

The inventors have further proceeded with the study and confirmed that where the curvature radius of the top of the arc constituting the substantially circular arc part of a cell is larger than that of the tangent circle formed at the edges of the two substantially linear parts on the circular arc part side of the cell, when the stent receives a bending load, stress and strain are almost uniformly distributed in the stent, and that the stent is not only excellent in a bending durability due to the most reduced load to the cell but also excellent in expansive uniformity because of decreased standard distension pressure, and therefore the present inventors have reached the present invention.

That is, the present invention provides a stent comprising a tubular body comprising a plurality of ring units being arranged in the axis direction and bridged by a connecting element, each of the ring units comprising a plurality of cells connected with each other, each of the cells having a substantially U-shaped form, comprising two substantially linear parts and a substantially circular arc part between the substantially linear parts, and opening toward one end along the axis direction, and the tubular body being capable of expanding in the radius direction from its inside, wherein the ring units comprise a first ring unit and a second ring unit, the first ring unit and the second ring unit being alternatively arranged so that the central axis of the stent is surrounded, the first ring unit comprising a first cell group in which a plurality of first cells are connected with each other in the circumferential direction, the second ring unit comprising a second cell group in which a plurality of second cells are connected with each other in the circumferential direction, and the first cells in the first ring unit being disposed oppositely to the second cells in the second ring unit adjacent to the first ring unit; the shapes of the first and second cells are axisymmetrical of the stent about the connecting element; pairs of the oppositely disposed first and second cells are only partly bridged by the connecting element, the connecting element creating connection between the substantially circular arc parts of the oppositely disposed cells; and wherein the curvature radius of the top of the arc constituting the substantially circular arc part of the cells in substantially all of the cells constituting the stent, is 1.1 to 1.5 times larger than the curvature radius of each of the tangent circles formed at the edges of two substantially linear parts of the cell.

In the above stent, the curvature radius of the top of the arc constituting the substantially circular arc part of the cell is preferably within the range of 1.2 to 1.4 times of the curvature radius of each of the tangent circles formed at the edges of two substantially linear parts of the cell.

In the above stent, the substantially linear parts of the cells bridged by the connecting element preferably have the same length with each other, and preferably are slightly longer than those of the unbridged cells. In general, the substantially linear parts of the cells bridged by the connecting element are longer than those of the unbridged cells by 10 to 25%, and where the length of the cell is 1.2 mm, the length of the connecting element is about 0.1 to 0.3 mm.

In the above stent, each of the ring unit may comprise 6 to 10 cells, and 1 to 3 cells out of the 6 to 10 cells preferably have a connecting element between disposed oppositely cells.

In the above stent, the connecting element may comprise a short linear material between substantially arc part parts in the oppositely disposed cells. In a preferable embodiment, the substantially circular arc parts of oppositely disposed cells are directly joined with each other to form the connecting element. In particular, the connecting element preferably shares both of vertexes of the central circular arc of the substantially circular arc parts of the oppositely disposed cells. Both the cell and the connecting element preferably have a constant width and thickness.

In the above stent, a material constituting the stent is preferably a cobalt chromium alloy or a stainless steel, or preferably a biodegradable metal or a biodegradable polymer. The biodegradable metal is preferably pure magnesium; a magnesium alloy; malleable iron; or an iron alloy.

Effect of the Invention

In the conventional stent, cells were bridged by the substantially S-shaped connecting element (connecting element 14 in FIG. 7). On the contrary, the stent according to the present invention has the following characteristics that (i) the stent eliminates the substantially S-shaped connecting element, that (ii) the oppositely disposed cells in the adjacent ring units are only partly bridged in the stent (i.e., not all of the oppositely disposed cells are bridged in the stent), and that (iii) the top of the arc which constitutes the substantially circular arc part in the substantially all cells has a curvature radius larger than that of tangent circles formed at the edges of the substantially linear part of the cells on the circular arc part side. As a result, the stress and strain applied to the cells are uniformly distributed, resulting in improved durability under a bending load without spoiling flexibility of the stent. Furthermore, according to the present invention, since some of the cells disposed oppositely are bridged by a connecting element in which the substantially circular arc part of the cell has the above-described configuration, the standard distension pressure of the stent is reduced to achieve a greatly improved durability under the above-mentioned bending load without spoiling expansibility.

DESCRIPTION OF THE EMBODIMENTS

Basic Shape of Stent

Figure 1:
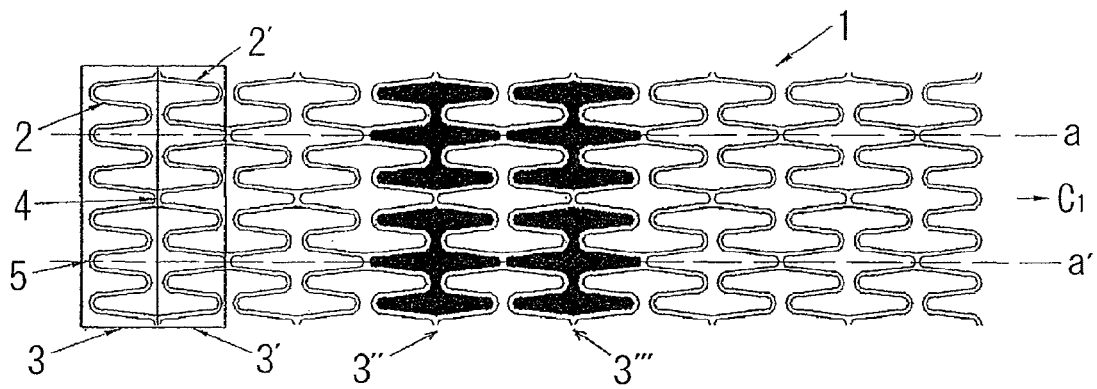
FIG. 1 is a plane view showing an example of the stent of the present invention.
Figure 2:
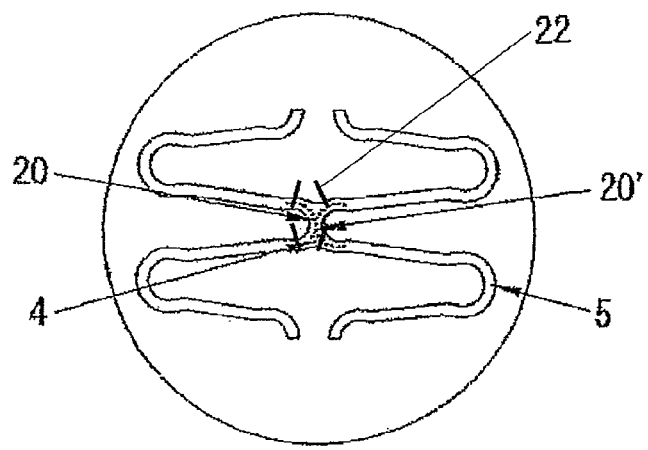
FIG. 2 is a partially enlarged view of FIG. 1.

Hereafter, the present invention is described in detail, referring to the drawings showing the concrete embodiment of the stent of the present invention. FIG. 1 is a plane view showing an example of the stent of the present invention. FIG. 2 is a partially enlarged view showing a connecting element of the stent 1 shown in the FIG. 1. As shown in FIG. 1, in the stent 1 of the present invention, cells 2 and 2' have a substantially U-shaped form which opens toward one end along the axis direction. A plurality of cells connected in the circumferential direction to surround the central axis C1 of the stent 1 to form ring units 3 and 3' so that a plurality of the ring units 3 and 3' arranged in the axis direction are bridged by the connecting element 4 so as to constitute a tubular body. This tubular body is expansible in the radius direction from its inside. Each of the cells with the above-mentioned U-shaped form comprises substantially linear parts and a substantially circular arc part 5.

In the stent of the present invention, the first and the second ring units 3 and 3' are alternatively connected to form a tubular body. The first ring unit 3 comprises a group of first cells in the way that a plurality of the first cells 2 are connected in the circumferential direction. The second ring unit 3' also comprises a group of second cells in the way that a plurality of the second cells 2 are connected in the circumferential direction. The first cells 2 and the second cells 2' are symmetrical about the connecting element 4. A plurality of cells in the ring unit 3 are disposed oppositely to a plurality of cells in the ring unit 3', and part of each of the cells are bridged by a connecting element 4 (partial link type). Since the oppositely disposed cells are only partly bridged (at not all of pairs), a stent having flexibility is obtained compared with the stent (all link type) where all pairs of the oppositely disposed cells are bridged. Preferably, the connecting elements 4 bridging the first ring unit 3 and the second ring unit 3' may be arranged together with the connecting elements 4' bridging the first ring unit 3'' and the second ring unit 3''' along lines a, a' in the axis direction C1 so that the cells in the expanded state may not be easily imbalanced in the axis direction at the time of expansion of the stent. Although tops of the substantially circular arc parts in the oppositely disposed cells may be bridged by an unbent short linear material with 0.1 to 0.3 mm in length, each of the substantially linear parts of the cells bridged by the connecting element 4 is preferably longer than the substantially linear parts of the unbridged cells so that each of the tops of the substantially circular arc parts 5 in the bridged cells contacts to be directly joined together. When oppositely disposed cells are bridged by a short linear material, bending load may cause the maximum stress in the central part of the linear connecting element which may be disadvantageous in respect of bending durability, whereas in directly bridged cells, the maximum stress will occur in four places (refer to symbol 22 in FIG. 2) of the circumference of the connecting element, resulting in reduced maximum stress so as to improve its bending durability. In this case it is preferable that the substantially linear parts of the cells are equal with each other and that both linear parts are a little longer than the substantially linear parts of the other unbridged cells from the viewpoint to obtain a homogeneous expansion of the stent. When the substantially linear parts of the cells have an equal length with each other, such cells can open in the same angle so as to support a blood vessel uniformly. Accordingly as shown in FIG. 1 among the oppositely disposed cells 2, 2', the cells 2, 2' bridged by the connecting element 4 have no space between cells, whereas a space is formed between the substantially circular arc parts of the unbridged cells 2, 2'. As a result, the substantially linear parts of the bridged cell are longer than the substantially linear parts of the unbridged cells by the length corresponding to the distance equivalent to this space. This slight existence of the space between the unconnected parts prevents oppositely disposed cells not only from overlapping, but also from being touched with each other when the stent is bent or compressed. In general, the substantially linear parts of the bridged cells by the connecting element are longer than those of the unbridged cells by about 10% to 25%. When the difference in length between the substantially linear parts of the cells bridged by the connecting element and the substantially linear parts of the unbridged cells is less than 10%, there are too little space between the unbridged cells 2 and 2' to achieve the above-mentioned effect. On the other hand, if the difference exceeds 25%, the space will be too large for supporting a blood vessel uniformly and therefore disadvantageous. Furthermore, if the length of the bridged cells is too longer than that of the unbridged cells, uniform expansion of the stent may be disadvantageously deteriorated so that the stress may be undesirably applied to the connecting element.

(Configuration of Substantially Circular Arc Part of Cell)

Figure 13:
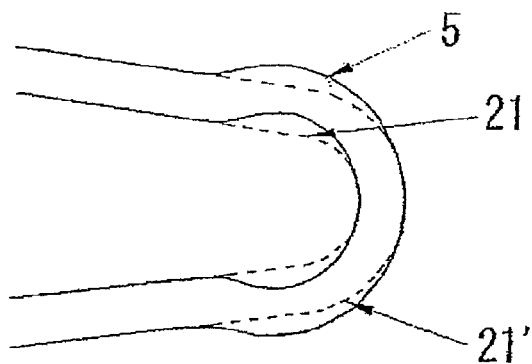
FIG. 13 is a schematic plane view of the tangent circles formed at the edges of the linear parts of the cell on the circular arc part side.

In the stent of the present invention, the curvature radius of the top of the arc constituting the substantially circular arc part 5 of the cell, which constitutes the stent, is 1.1 to 1.5 times larger, preferably 1.2 to 1.4 times larger, than the curvature radius of the tangent circles 21, 21' formed at the edges of two substantially linear parts in the cells 2, 2' on the circular arc part side (see FIG. 13). Because of this feature, the level of the maximum stress generated at the top of the substantially circular arc part due to a bending load will be reduced so that the durability will be improved under repetitive bending loads, and that stress and strain are uniformly distributed at the time of expansion to achieve a good uniform expansion of the stent and to increase safety rate of the expansion operation due to the lower standard distension pressure compared with that in the conventional stent. It is difficult to reduce the level of the maximum stress generated at the top of the substantially circular arc part when the curvature radius of the substantially circular arc part is 1.1 times lower than that of the tangent circle 21. Moreover, if the curvature radius of the substantially circular arc part is 1.5 times larger than that of the tangent circle 21, the stress will occur at the boundary of the substantially linear part and the substantially circular arc part of the cell so that the stent will fail to improve durability effect. Furthermore, when the top of the substantially circular arc part has a curvature radius of 1.5 times larger than that of the tangent circle 21, such large top will make the stent undesirable because the circular arc parts may interfere with each other at the time of stent crimping. The bearing capacity of the stent in the radius direction will be greater when the cells 2, 2' has an obtuse angle to the central axis C1 after expansion of the stent. Moreover, the bearing capacity of the stent in the radius direction will be also greater when the angle $\theta$ constituted by two substantially linear parts of the cell after expansion is close to 120°. That is, the stent is designed so that the angle $\theta$ after expansion of the cell may be preferably at least 50° or larger when it expands to at least 2.5 mm in diameter.

(Dimension of Stent)

In the present invention, the size of the stent (length and diameter of unexpanded stent) is not particularly limited to a specific one, and may be in the same range of the conventionally used stents. The length and diameter of unexpanded stent may be preferably within the range between about 9 mm and about 40 mm and the range between about 0.8 mm and about 2 mm, respectively. The length of the ring unit of the stent is preferably within the range between about 0.5 mm and about 3.0 mm. The length of the connecting element (the length of the space between the unbridged cells in the axis direction) may be preferably within the range between about 0.05 mm and about 1 mm, and more preferably within the range between about 0.1 mm and about 0.3 mm.

Moreover, the number of arranged cells 2, 2' in the circumference direction is preferably not less than 4 pieces. Further, when the stent has a diameter of not smaller than 3.0 mm after expansion, the number of arranged cells 2, 2' in the circumference direction is preferably not less than 6 pieces, usually within the range between 6 pieces and 12 pieces. Moreover, as to the ring units 3 and 3', the number of pairs of ring units 3 and 3' to be arranged in the stent is preferably not less than 6 pairs, usually within the range between 6 pairs and 12 pairs in the longitudinal direction of the stent, or the stent axis direction. Further, the stent may comprise not less than 3 pairs (usually 4 to 8 pairs) of ring units 3 and 3' per 10 mm in the stent axis direction, and when the stent has a desired diameter after expansion (the standard diameter such as diameter of 3.0 mm or 4.0 mm), for example, the stent is preferably designed so that the angle $\theta$ formed by two substantially linear parts of the cell after expansion form is, as stated previously, at least 50°, usually within the range between 60° and 120°. Although it is effective for a stent to be designed to have a desired diameter over 120° in order to improve bearing capacity of the stent in the radius direction, such stent may have a problem that the deformation amount of the substantially circular arc part 5 becomes too large. Moreover, such a stent may not be preferable because it may have problems such that overall shortening (fore-shortening) of the stent after expansion is too large and that positioning at the time of stent implantation becomes too difficult.

Figure 10:
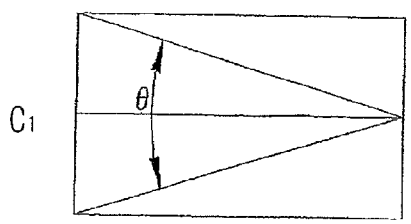
FIG. 10 is a conceptual view of a strut which constitutes a cell.

It is preferable that, as shown in FIG. 10, the strut (two linear parts) of cells 2 and 2' is formed symmetrically in the diameter direction to the central line C1 of the stent axis direction. Moreover, the thickness of the cell 2 is usually constant in the stent 1. In general, the cells 2 of the stent 1 made of cobalt chromium alloy may have a width and a thickness of usually within the range between 80 and 110 µm and between 70 and 90 µm, respectively. In the stent 1 made of stainless steel, the width and thickness of the cells 2 are usually within the range between 80 and 150 µm and between 100 and 150 µm, respectively. In the present invention, it is preferable that the width and thickness of the cells 2 are constant in the ring unit 3 as well as in the connecting element 4. The stent comprising cells 2 with a constant width and thickness makes easy to have a well-controlled size at the time of processing and polishing. Moreover, the stent comprising cell 2 with a constant width and thickness also has a constant cross-section area so that the bending moment in the same direction becomes comparable at every portion, resulting in tendency that the flexibility of the stent is no longer affected by the direction. In particular, the stent comprising cells disposed oppositely to be bridged directly (i.e., linked) and having overlapped vertexes of the circular arc parts of the oppositely disposed cells 20, 20' with a constant thickness and width to form the connecting element is preferably used because of improved uniform expansion (see FIG. 2).

The stent comprising the connecting element 4 as mentioned above can greatly improve durability and have an advantage that there is no reduction in flexibility and expansibility because the stress does not concentrate on the connecting element 4. Moreover, since not all of the oppositely disposed cells 2 and 2' are bridged by the connecting element 4 (i.e., the stent is a partial link type), even if the diameter of the stent 1 is reduced at the time of the delivery to a blood vessel, the cells 2 and 2' are not sterically overlapped with each other in the radius direction of the stent.

In the stent 1 of the present invention illustrated in FIGS. 1 and 2, the stent needs to have, in the circumferential direction of the stent, at least one connecting element 4 between the cells 2, 2' constituting each of the ring units 3, 3'. As mentioned above, since the number of cells arranged in the circumferential direction is different according to the diameter of the stent, the number of connecting elements may be appropriately decided depending on the number of cells to be arranged. When the stent has a diameter of 3 to 9 mm and comprises 6 to 10 cells in the circumferential direction, the number of the connecting elements is preferably within the range between 1 piece and 3 pieces. In the present invention, a part of (not all of) pairs in the oppositely disposed cells 2, 2' is bridged to form a connecting element therebetween, and the other cells 2, 2' remains to be unbridged with each other as an unconnected part. This unconnected part makes the entire stent 1 more flexible as well as easier to be conveyed to the branched blood vessel. Further, since the stress to the arc portion which forms a connecting element is distributed widely, the stent has an improved durability compared with the stent comprising connecting elements arranged in sequence among all of the oppositely disposed cells.

The stent of the present invention is manufactured from a metal pipe comprising stainless steels, such as SUS316 grade; shape memory alloys, such as, a Ni—Ti alloy, and a Cu—Al—Mn alloy; a titanium alloy; a tantalum alloy; a cobalt chromium alloy; or the like. Moreover, the stent of the present invention may be manufactured from a biodegradable metal, the metal which can be degraded in the living body. Examples of the biodegradable metals include pure magnesium, a magnesium alloy, pure iron, an iron alloy, and the like. The preferable magnesium alloy may include magnesium as a principal component and at least one element selected from the biocompatible element group consisting of Zr, Y, Ti, Ta, Nd, Nb, Zn, Ca, Al, Li, and Mn. Such a preferable magnesium alloy may comprise, for example, 50 to 98% of magnesium, 0 to 40% of lithium (Li), 0 to 5% of iron and 0 to 5% of other metal(s) or rare earth element(s) (e.g., cerium, lanthanum, neodymium, praseodymium). The preferable iron alloy may include iron as a principal component and at least one element selected from the biocompatible element group consisting of Mn, Co, Ni, Cr, Cu, Cd, Pb, Sn, Th, Zr Ag, Au, Pd, Pt, Re, Si, Ca, Li, Al, Zn, Fe, C, and S. Such a preferable iron alloy may comprise, for example, 88-99.8% of iron, 0.1 to 7% of chromium, 0 to 3.5% of nickel, and not more than 5% of other metal(s).

Furthermore, the stent of the present invention may be also manufactured from a biodegradable polymer, such as a polylactic acid, a polyglycol acid, poly (lactic acid-glycolic acid), poly (lactic acid-ε-caprolactone), and poly (glycolic acid-ε-caprolactone); or a composite biodegradable polymer in which a biodegradable high-toughness polymer, such as poly (succinic acid butylene) is dispersed in a biodegradable matrix polymer, such as a polylactic acid, etc. These biodegradable polymers may be subjected to drawing and/or orientation. Furthermore, the biodegradable polymer may coat the surface of the metal which is degradable in the living body.

The stent of the present invention having such a configuration as mentioned above may be integrally formed by laser machining. The manufacture process by laser machining is illustrated as below. First, a tool pass by laser machining is created with CAM based on the configuration data of the designed stent. The tool pass is specified taking into consideration of that the stent configuration is maintainable after the laser cut and that scraps do not remain. Next, laser machining is operated on a thin-walled tube made from metal or polymer. Processing conditions are selected for the purpose of a high speed and quality processing with reduced burrs.

After a network configuration is formed by laser-cutting processing, electrolytic polishing is performed to finish the surface to be glossed as well as to smooth edge parts. In the case of the stent made from a cobalt chromium alloy, the post-processing step is of importance after laser-cutting processing. The stent after laser-cutting processing is subjected to acid liquid so that the metal oxide on the cutting plane is dissolved, followed by electrolytic polishing. In the electrolytic polishing, a stent and a metal plate, such as stainless steel, are dipped into an electrolyte, and are connected with each other through a DC power. By applying voltage to the stent as an anode and the metal plate as a cathode, the stent is effectively polished after the surface of the stent is dissolved as the anode. In order to acquire the suitable polish effectiveness, it is necessary to examine composition of an electrolyte and current conditions to be applied.

Since the stent manufactured by the above-mentioned laser process can have the network structure just as designed, the stent to be provided has high flexibility and bearing capacity of the stent in the radius direction and also inhibits fore-shortening and flare phenomenon because of increased blood vessel expansibility, and further deters cutting of cells or others in use.

EXAMPLES

Hereinafter, the present invention will be demonstrated by way of some examples that are presented only for the sake of illustration, which are not to be construed as limiting the scope of the present invention. It should be noted that in the following Examples and Comparative Examples, expansion pressure, bending durable time, flexibility, fore-shortening value, recoil value, and the maximum strain were evaluated in the following manners.

(Measurement of Expansion Pressure)

A stent with diameter of 3.0 mm was inserted into a silicone tube with an inner diameter of 3.0 mm, and an outer diameter of 4.0 mm. Then, physiological salt solution was poured into the silicone tube, and the expansion pressure when expanding the inner diameter of the stent by a balloon to 3 mm was measured.

(Measurement of Flex-Endurance Time)

Figure 11:
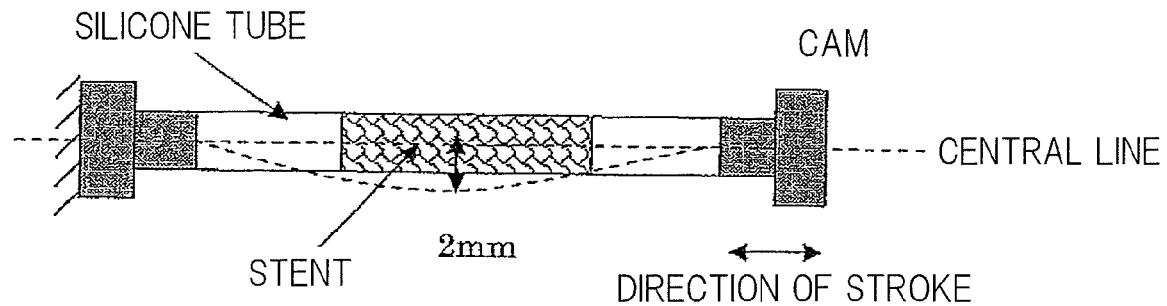
FIG. 11 is a schematic view showing a sample for bending test.

As shown in FIG. 11, both ends of a silicone tube were fixed in such a way that the left and right ends of the tube were fixed to the stage side and the cam, respectively. Subsequently, the cam was reciprocated by rotation of a motor so that the center portion of the stent was flexed at the width of 2.0 mm to the down side as the center of the silicone tube was bent. The bending operation of the center portion of the stent inserted into the silicone tube was repeated, and the endurance time until rupture of the stent was measured.

(Evaluation of Flexibility)

Flexural strength was measured by the four-point bending method to evaluate flexibility of a stent.

(Measurement of Fore-Shortening Value)

A stent was inserted into a silicone tube with inner diameter of 3.0 mm and outer diameter of 4.0 mm. Then, physiological salt solution was poured into the silicone tube, and the inner diameter of the stent was expanded to 3 mm. The length of the stent after expansion was measured, and the rate of reduction to the length of the stent before expansion was calculated to regard the rate as fore-shortening value.

(Calculation of Recoil Value)

A stent was inserted into a silicone tube with inner diameter of 3.0 mm and outer diameter of 4.0 mm. Then, physiological salt solution was poured into the silicone tube, and the inner diameter of the stent was expanded to 3 mm by a balloon. Then, the balloon was removed and the inner diameter of the stent after balloon removal was measured to calculate recoil value of the stent by the following formula (1).

[Formula 1]

$$\text{Recoil value} = \frac{(\text{Diameter at expansion}) - (\text{Diameter after balloon removal})}{(\text{Diameter at expansion})} \times 100 \quad (1)$$

(Measurement of the Maximum Strain)

Strain generated to each part of a stent in a series of processes from contraction of the stent diameter by a crimper to placement of the stent into a blood vessel by balloon inflation was evaluated from the viewpoint of the material strength using the analysis by computer simulation. The stent finite element model was constructed, and suitable material characteristics and features were inputted. After the stent was contracted to have an outer diameter of 1.0 mm, the stent was expanded to have an inner diameter of 3.0 mm so as to detain the stent in the blood vessel, and the maximum strain generated in the series of processes was calculated.

Figure 12:
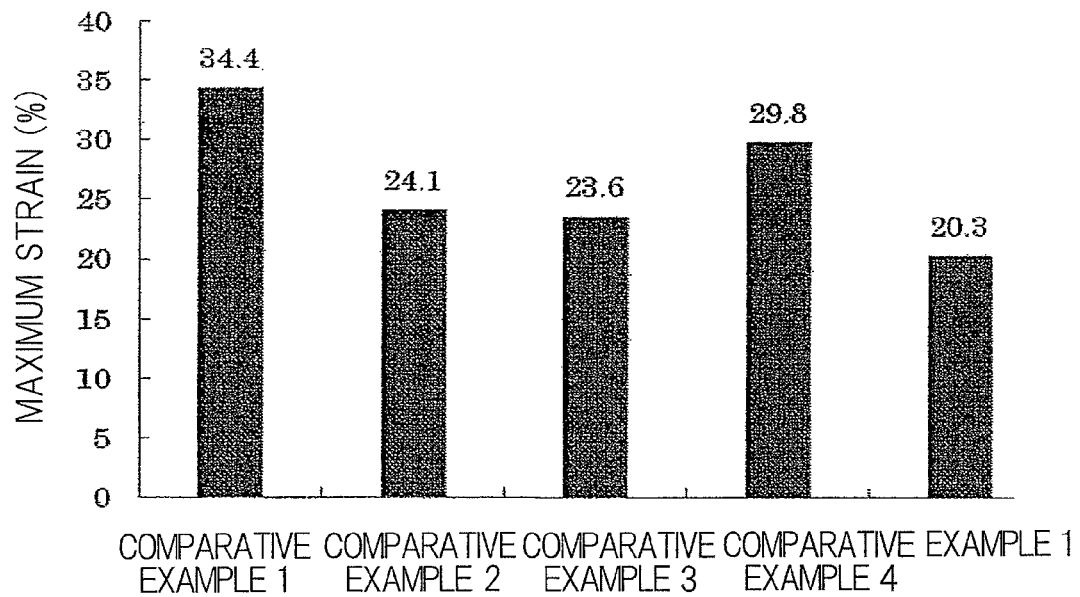
FIG. 12 is a graph showing the maximum strain of the stents of Examples and Comparative Examples.

A stent (Example 1) shown below was used as a stent of the present invention to compare with stents of Comparative Examples 1 to 4 shown below. The result was shown in Table 1 and FIG. 12. It should be noted that each stent used in Example 1 and Comparative Examples 1 to 4 made from a cobalt chromium alloy and has a length of 17.4 mm, an inner diameter of 1.0 mm at the time of contraction, an inner diameter of 3.0 mm at the time of expansion. The In a stent, the cells 2, 2' and the connecting element 4 therebetween have a constant width of 100 μm and a constant thickness of 70 μm.

Example 1

In the stent of Example 1 shown in FIG. 1, all the cells regardless of existence or nonexistence of connecting element have a curvature radius of the top of the arc constituting the substantially circular arc part 5 of R0.20 μm which is 1.3 times of the curvature radius of the tangent circle (R0.15 μm) formed at the substantially linear part 2 (FIG. 2).

(The length of one cell forming an unbridged part: 1.2 mm, the length of one cell forming a connecting element: 1.3 mm, the number of the cells in one ring unit: 6)

Comparative Example 1

Figure 7:
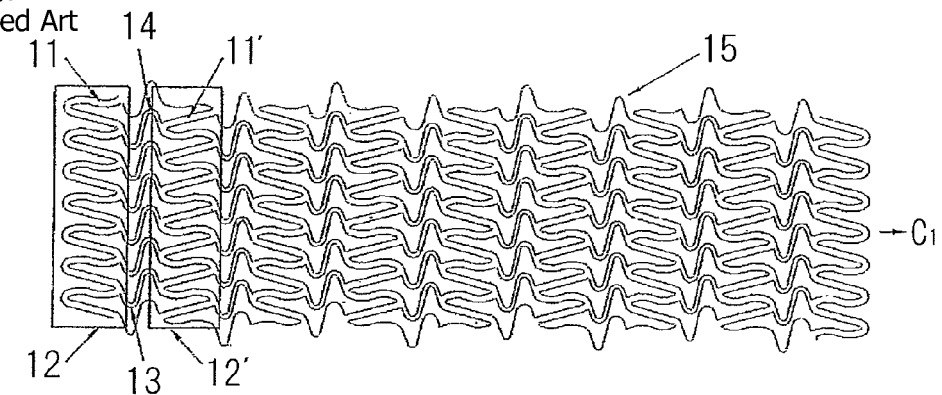
FIG. 7 is a plane view showing all-linked conventional stent.
Figure 8:
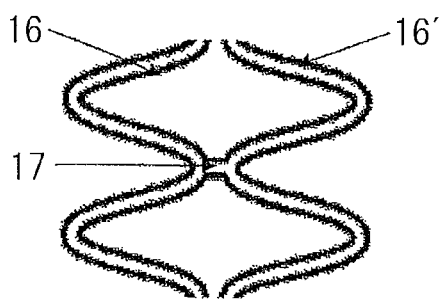
FIG. 8 is a schematic plane view showing a connecting element between ring units of the stent available from another company.
Figure 9:
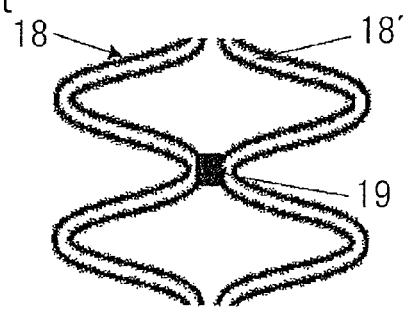
FIG. 9 is a schematic plane view showing a connecting element between ring units of the stent available from another company.

The conventional stent (all linked stent) of Comparative Example 1 shown in FIG. 7 comprises a first ring unit 12 and a second ring unit 12' alternately. The first ring unit 12 consists of a first cell 11 group which comprises a plurality of first cells 11 to be connected in the circumferential direction. The second ring unit 12' consists of a second cell 11' group which comprises a plurality of second cells 11' having an axisymmetrical configuration with the first cells about the diameter direction. All cells disposed oppositely are bridged to form a substantially tubular body. All of the adjacent ring units 12 and 12' are bridged by the connecting element 14. The ring units 12 and 12' can be expanded from the inside of the tubular body to the circumferential direction. The ring unit 12 comprises a plurality of cells 11 connected with each other in the circumferential direction. Two or more ring units are arranged so that the central axis C1 of the stent 15 is surrounded.

(The length of one cell: 1.2 mm, the length of a connecting element: 0.6 mm, and the number of the cells in one ring unit: 6)

Comparative Example 2

Figure 3:
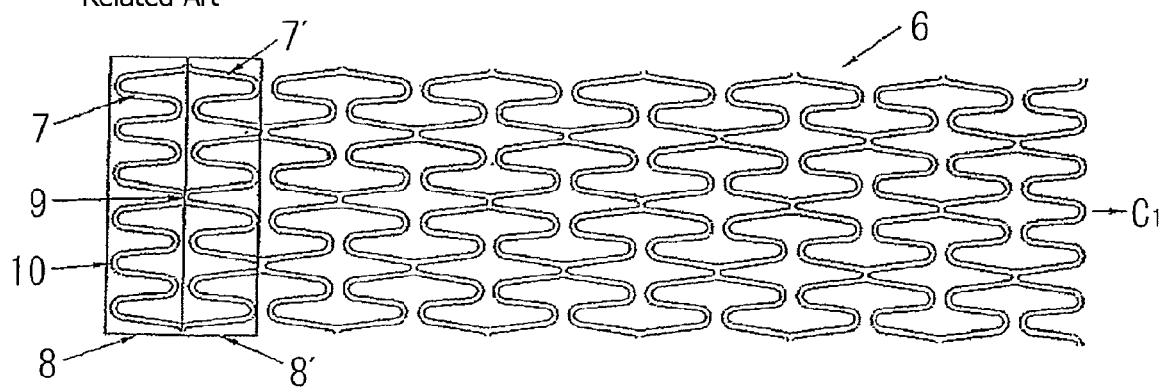
FIG. 3 is a plane view showing an example of a partially linked conventional stent.
Figure 4:
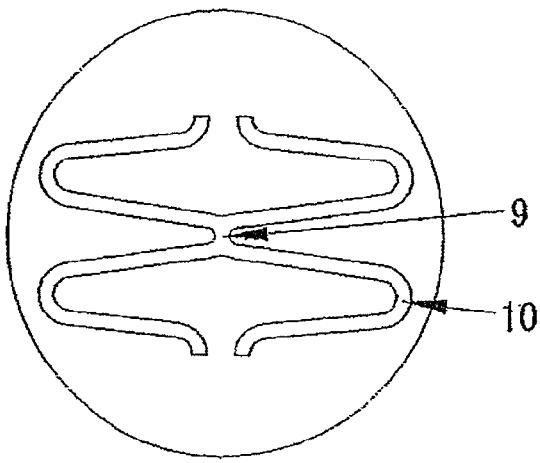
FIG. 4 is an enlarged view of FIG. 3.

In the stent of Comparative Example 2 shown in FIG. 3, the curvature radius of the top of the arc which constitutes the cell circular arc part 10 is R0.15 μm (FIG. 4).

(The length of one cell: 1.2 mm, the length of one cell forming the connecting element: 1.3 mm, the number of cells in one ring unit: 6)

Comparative Example 3

Figure 5:
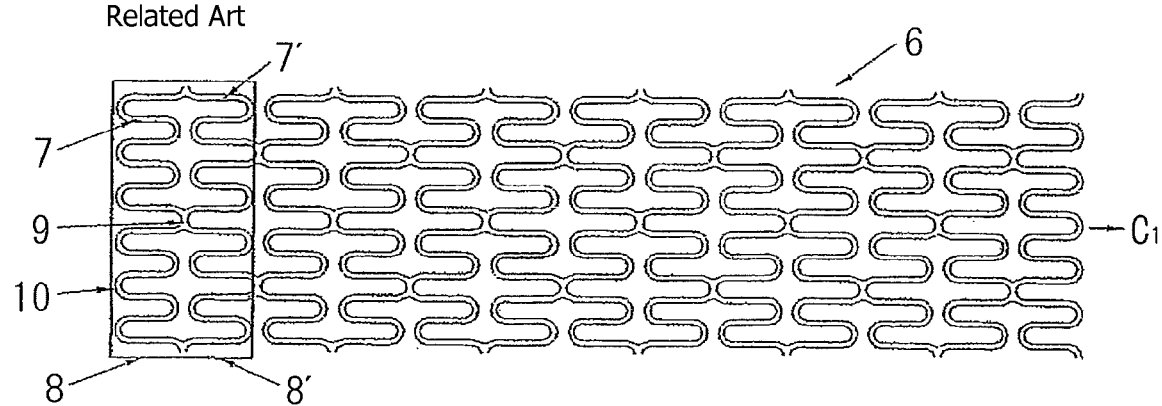
FIG. 5 is a plane view showing another example of a partially linked conventional stent.
Figure 6:
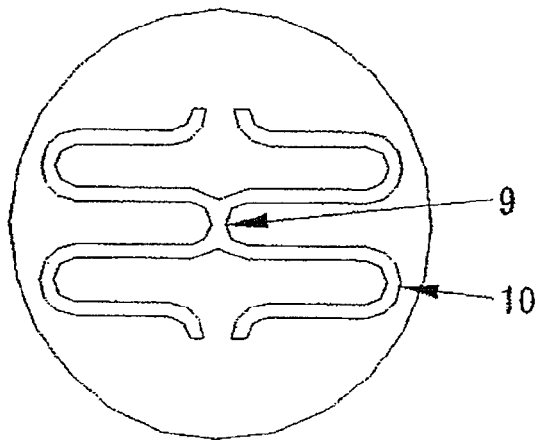
FIG. 6 is an enlarged view of FIG. 5.

In the stent of Comparative Example 3 shown in FIG. 5, the curvature radius of the top of the arc which constitutes the cell circular arc part 10 is R0.20 μm (FIG. 6).

(The length of one cell forming an unbridged part: 1.2 mm, the length of one cell forming a connecting element: 1.3 mm, the number of cells in one ring unit: 6)

Comparative Example 4

Figure 14:
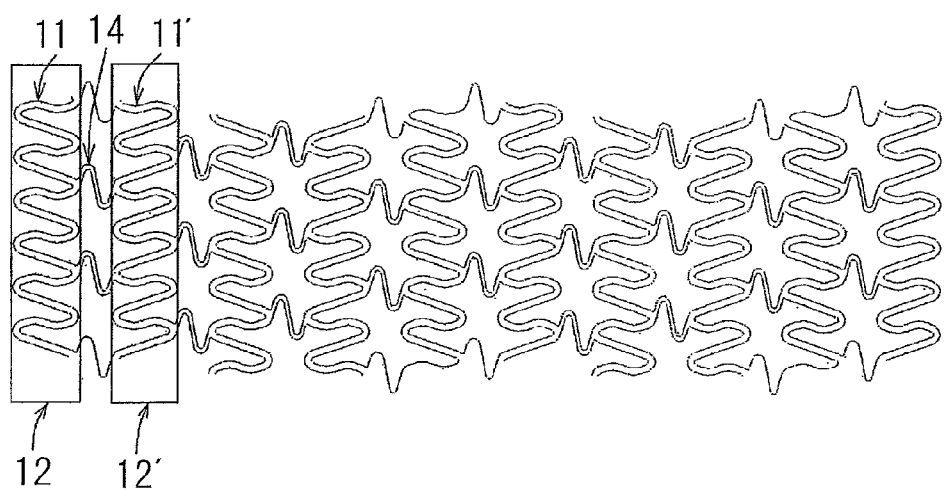
FIG. 14 is a plane view showing another example of a partially linked stent.

The stent of Comparative Example 4 shown in FIG. 14 is a partial link type comprising connecting elements alternatively between the ring units 12 and 12' disposed oppositely, instead of the conventional all linked type stent of Comparative Example 1 shown in FIG. 7 in which all of the oppositely disposed cells 11, 11' in the ring units 12 and 12' are bridged by substantially S-shaped connecting elements 14.

As shown in Table 1, the results reveal that the durabilities of the partially linked stents (Example 1, Comparative Examples 2, 3, and 4) are larger than that of the all linked stent (Comparative Example 1). As this reason, it is surmised that the partially linked stents excel the all linked stent in bending durability probably because deformation of cell space (i.e., large freedom of the movement due to few restraining points) reduces the load applied to the link. In comparison of partially linked stent group, the durability of Example 1 is larger compared to those of other partially linked stents. As this reason, it is surmised that the bending durability of Example 1 is excellent because Example 1 has the lower maximum strain when a bending load is applied (see FIG. 12), resulting in the smallest load to be applied to the cell. Further, Example 1 had a standard distension pressure of 8 atms which was lower than both of the standard distension pressure 9 atm of Comparative Examples 2 and 3, and therefore it was confirmed that Example 1 was also excellent in expansion homogeneity and flexibility. Furthermore, since Example 1 has a fore-shortening value, a recoil value, etc. which are equivalent to those of the conventional stent, Example 1 is a stent excellent in the balance of durability and the performance capability.

In designing the stent of the present invention, it is important that the stent has a structure that the maximum stress and strain of the stent is minimized and that the stent has a substantially constant stress and strain on each point along the cell linear part as well as cell connecting element 4. FIG. 2 is an enlarged view of a circular arc part 5 and a connecting element 4 of the cell in the stent of Example 1. Such a configuration is excellent in durability, and capable of providing a stent having a substantially uniform stress and strain on the arc part 5 and a connecting element 4 due to uniform deformation of the cells when a bending load is applied to the stent.

As mentioned above, the stent of the present invention has a structure in which the circular arc part 5 of the cell and the connecting element 4 receive comparatively lower stress and strain than the bending element between the cells of Comparative Example 1 and the circular arc part 10 and the connecting element 9 of Comparative Examples 2 and 3. Further, the stent of the present invention is excellent in bending durability and has an excellent bending flexibility and an improved homogeneity for expansion because (i) the top of the arc which constitutes the cell circular arc part 5 has a curvature radius of 1.1 to 1.5 times larger than that of each of the tangent circles formed at the edge part of the substantially linear part of the cells 2, 2' on the circular arc part side and (ii) minimization of the maximum stress and strain is attained by bridging some of cells with the connecting element 4.

INDUSTRIAL APPLICABILITY

Since the present invention can provide stents having a structure excellent in durability to withstand a bending load

TABLE 1

|  | Comparative Example 1 (FIG. 7) (All link type) | Comparative Example 2 (FIG. 3) (Partial link type) | Comparative Example 3 (FIG. 5) (Partial link type) | Comparative Example 4 (FIG. 14) (Partial link type) | Example 1 (FIG. 1) (Partial link type) |
|---|---|---|---|---|---|
| Standard distension pressure (atm) | 8 | 9 | 9 | 8 | 8 |
| Bending frequency (Hz) | 5 | 5 | 5 | 5 | 5 |
| Flex-endurance time (h) | 1.0 | 102 | 102 | 6.0 | 400 |
| Flexibility (N · mm$^2$) (Flexural strength) | 31 | 8.0 | 8.0 | 8.0 | 4.0 |
| Fore-shortening value (%) | 3.6 | 3.5 | 2.1 | 2.1 | 5.2 |
| Recoil (%) | 4.5 | 3.9 | 3.9 | 3.6 | 2.7 | and flexibility, such stents of the present invention greatly contributes to stent manufacture technology and also have a great impact to industrial applicability. Furthermore, since stents of the present invention can be integrally manufactured by laser processing, availability of such stents on industry is also large from this point.

As mentioned above, the preferred embodiments of the present invention are illustrated, but it is to be understood that other embodiments may be included, and that various additions, other changes or deletions may be made, without departing from the spirit or scope of the present invention.

EXPLANATIONS OF LETTERS OR NUMERALS

1: Stent
2, 2': Cell
3, 3', 3", 3'": Ring unit
4: Connecting element
5: Circular arc part of cell
6: Conventional stents (Comparative Examples 2 and 3)
7, 7': Cell
8, 8': Ring unit
9: Connecting element
10: Circular arc part
11, 11': Cell
12, 12': Ring unit
13: Bending part
14: Connecting element
15 Conventional stent (Comparative Example 1)
16, 16': Cell
17: Connecting element
18, 18': Cell
19: Welding part
20, 20': Central circular arc
21, 21': Tangent circle
22: Point generating the maximum stress
a, a': Lines of connecting element
C1: Central axis of stent

What is claimed is:

1. A stent comprising a tubular body comprising a plurality of ring units being arranged in a longitudinal axis direction and bridged by a connecting element, each of the ring units comprising a plurality of cells connected with each other, each of the cells having a substantially U-shaped form, comprising two substantially linear parts and a substantially circular arc part between the substantially linear parts, and opening toward one end along the longitudinal axis direction, the tubular body being capable of expanding in the radius direction from its inside, wherein the ring units comprise a first ring unit and a second ring unit, the first ring unit and the second ring unit being alternatively arranged so that the central axis of the stent is surrounded, the first ring unit comprising a first cell group in which a plurality of first cells are connected with each other in the circumferential direction, the second ring unit comprising a second cell group in which a plurality of second cells are connected with each other in the circumferential direction, and the first cells in the first ring unit being disposed oppositely to the second cells in the second ring unit adjacent to the first ring unit to form pairs of oppositely disposed first and second cells;

the shapes of the first and second cells are axisymmetrical of the stent about the connecting element;

only a portion of the pairs of the oppositely disposed first and second cells are bridged by the connecting element, such that a remaining portion of the pairs are unbridged, the connecting element creating a connection between the substantially circular arc parts of the oppositely disposed cells;

the curvature radius of the top of the arc constituting the substantially circular arc part of the cells in substantially all of the cells constituting the stent, is 1.1 to 1.5 times larger than the curvature radius of each of the tangent circles formed at the edges of the two substantially linear parts of the cell on the circular arc part side;

the substantially linear parts of the cells bridged by the connecting element have the same length with each other, and the substantially linear parts of the cells bridged by the connecting element are longer than the substantially linear parts of the unbridged cells by 10 to 25%; and the bridged pairs of oppositely disposed first and second cells are bridged directly and have overlapped vertexes of the circular arc parts of the oppositely disposed cells with a constant thickness and width to form the connecting element.

2. The stent as claimed in claim 1, wherein the curvature radius of the top of the arc constituting the substantially circular arc part of the cell is within the range of 1.2 to 1.4 times of the curvature radius of each of the tangent circles formed at the edges of two substantially linear parts of the cell on the circular arc part side.

3. The stent as claimed in claim 1, wherein each of the ring unit comprises 6 to 10 cells, and 1 to 3 cells out of the 6 to 10 cells have a connecting element between disposed oppositely cells.

4. The stent as claimed in claim 1, wherein the substantially circular arc parts of oppositely disposed cells are directly joined with each other to form the connecting element.

5. The stent as claimed in claim 1, wherein both the linear part and the circular arc part of the cells have a constant width and thickness.

6. The stent as claimed in claim 1, wherein a material constituting the stent is a cobalt chromium alloy or a stainless steel.

7. The stent as claimed in claim 1, wherein a material constituting the stent is a biodegradable metal or a biodegradable polymer.

8. The stent as claimed in claim 7, wherein the biodegradable metal is selected from the group consisting of pure magnesium; a magnesium alloy; malleable iron; or an iron alloy.

* * * * *